United States Patent [19]
Newmark

[11] Patent Number: 5,645,852
[45] Date of Patent: Jul. 8, 1997

[54] BUTYRIC ESTER CYTO-DIFFERTIATING AGENTS

[75] Inventor: Harold L. Newmark, Maplewood, N.J.

[73] Assignee: Sloan-Kettering Institute for Cancer Research, New York, N.Y.

[21] Appl. No.: 527,744

[22] Filed: Sep. 13, 1995

Related U.S. Application Data

[63] Continuation of Ser. No. 150,512, Nov. 10, 1993, abandoned.

[51] Int. Cl.$^6$ .................................................. A61K 31/215
[52] U.S. Cl. ........................... 424/439; 514/546; 560/263
[58] Field of Search ............................. 424/439; 514/506, 514/546; 560/263

[56] References Cited

U.S. PATENT DOCUMENTS

| | | | |
|---|---|---|---|
| 4,816,450 | 3/1989 | Bell | 514/25 |
| 5,025,029 | 6/1991 | Perrine | 514/381 |
| 5,185,436 | 2/1993 | Villa et al. | 536/4.1 |
| 5,200,553 | 4/1993 | Nudelman et al. | 560/263 |
| 5,258,197 | 11/1993 | Wheeler | 426/607 |

OTHER PUBLICATIONS

Wilkinson JBC 268 #4, p. 2844, Feb. 1993.
Deschner, E.E., et al., *Cancer Letters*, 52: 79–82, 1990.
Lea, M.A., et al., *Anticancer Research*, 13: 145–150, 1993.
Boffa, L.C., et al., *Cancer Research*, 52: 5906–5912, Nov. 1, 1992.
Planchon, P. et al., *J. Pharm. Sci.*, 82: 1046–1048, Oct. 1993.
Perrine, S.P., et al., *Experientia, Birkhauser Verlag Basel*, 49: 133–137, 1993.
Blau, C.A., et al., *Blood*, 81: 529–537, Jan. 1993.
Daniel, P., et al., *Clinica Chimica Acta*, 181: 255–264, 1985.
Perrine, S.P., et al., *New Eng. J. Med.*, 328: 81–86, Jan. 1993.
Miller A. et al., *Eur. J. Cancer Clin. Oncol.*, 23: 1283–1287, 1987.
Novogrodsky, A. et al., *Cancer*, 51: 9–14, Jan. 1993.

*Primary Examiner*—Gollamudi S. Kishore
*Attorney, Agent, or Firm*—John P. White

[57] ABSTRACT

This invention provides a method of inducing cell differentiation in a subject and methods of treating leukemia, thalassemia, or sickle cell anemia by administration to the subject of one or more oral bolus doses of a pharmaceutical composition comprising an effective amount of one or more butyryl glycerides and a pharmaceutically acceptable carrier. This invention also provides a method of treating a surface or skin disorder in a subject by topical administration to the subject of a pharmaceutical composition comprising an effective amount of one or more butyryl glycerides and a pharmaceutically acceptable carrier.

3 Claims, 1 Drawing Sheet

BUTYRIC ESTER CYTO-DIFFERTIATING AGENTS

This is a continuation of application Ser. No. 08/150,512, filed Nov. 10, 1993, now abandoned.

BACKGROUND OF THE INVENTION

Throughout this application, various publications are referenced in parentheses. Full citations for these publications can be found immediately preceding the claims. The disclosures of these publications in their entirety are hereby incorporated by reference into this application in order to more fully describe the state of the art as known to those skilled therein as of the date of the invention described and claimed herein.

It has long been well known that the salts of butyric acid, particularly the sodium salt, act in vitro on many abnormal or transformed cell lines to cause these cells to change to a more normal state, including phenotype and function. This "differentiation" action is also shown by a number of agents with no readily obvious structure-activity relationship. In vitro, butyrate acts on some cancer or leukemia cancer cell lines such as HT-29, or HL-60 in this fashion, when maintained at concentrations of about 0.3 to 5 millimolar (mM). Desirable changes of the aberrant blood cells of sickle cell anemia and thalassemia can be obtained in vitro at lower concentrations of about 0.05 mM [Perrine S. P., et al., *N. Engl. J. Med.*, Vol. 328, pages 81–86, (1993); Perfine, S. P., et al., *Blood*, Vol. 74, pages 454–459 (1989)].

Attempts to utilize butyrate salts in therapy have not generally been successful. An early attempt at using intravenous infusions of sodium butyrate at 500 mg/kg body weight per day for several days produced only a short-lived remission in a child with leukemia [Novogrodsky, A., et al., *Cancer*, Vol. 51, pages 9–14]. A larger study [Miller, A. A., et al., *Eur. J. Cancer Clin. Oncol.*, Vol. 23, pages 1283–1287 (1987)], using the same infusion rate showed no clinical response, but also demonstrated that the infused butyrate had a very short metabolic half-life of about 6 minutes, resulting in peak blood levels below 0.05 mM, considered ineffective for leukemia. Higher rates of intravenous infusions could not be considered because of the risk of toxicity from sodium overload, and achieved success in treating thalassemia and sickle cell patients by continuous intravenous infusions of 500 mg/kg/day or higher doses, if needed, for several days. In these studies also, blood levels of butyrate did not exceed 0.05 mM and the butyrate was apparently rapidly metabolized [Perrine, et al. (1993)].

Butyrate is a normal metabolite supplied to mammals from 2 main sources. It is produced as a major product of bacterial fermentation of unabsorbed carbohydrate in the colon, and reaches concentrations of up to 20 mM in the colon and feces of animals and man [Cummings, J. H., Gut, Vol. 22, pages 763–779 (1981)]. The other source of butyric acid is the diet, where it is present at low levels in many fruits and vegetables, but its richest source is from milk fat (butter, etc.) which contains 3–4% butyrate in a complex of glycerides, or esters of glyceryl [Composition of Foods: Dairy and Egg Products (1976), U.S. Dept. Agriculture Handbook 8-1, Washington, D.C.]. However, when butyryl triglyceride (tributyrin, or glyceryl tributyrate) was used at 5% of the feed in our laboratories as means of preventing chemically induced colon cancer in mice, it was ineffective [Deschner, et al., *Cancer Letters*, Vol. 52, pages 79–82 (1990)] although it did not produce the promoting or cancer increasing effect of the sodium salt used by others in equivalent intake [Freeman, H. J., *Gastroenterology*, Vol. 91, pages 596–602 (1986)]. Apparently, the high sodium intake acted as a cancer promoter [Freeman, (1986)], and the butyrate was metabolized too rapidly to be preventive.

The object of this invention, therefore, is a method of administering butyric ester compounds to a subject suffering from a disease against which butyrate would be effective, which would provide for an effective amount of butyrate to remain in the subject's system for an effective period of time and thereby treat the disease.

It was hypothesized that butyryl glycerides, including but not limited to tributyrin, several possible dibutyl glycerides and monobutyrin such as the 1-butyryl glyceryl, which are essentially non-charged, i.e., non-anionic, substances of comparatively low molecular weight, administered in an oral bolus dose, are potentially easily absorbable directly into the stomach and upper gastrointestinal tract. They can then enter into the lipid transport system, and be slowly hydrolyzed by the lipases in serum and possibly liver. These lipases are generally slower than the gastric and pancreatic lipases of the G.I. tract. The net effect of oral bolus administration would be to maximize systemic absorption, such as from the stomach, of one or more of the glycerides, as well as butyric acid, which would then act as a "reservoir" of butyrates for slow release within the blood stream. The unexpected activity of the glycerides per se as differentiating agents could add significant therapeutic effect to the total.

SUMMARY OF THE INVENTION

This invention provides a method of inducing cell differentiation in a subject by administration to the subject of one or more oral bolus doses of a pharmaceutical composition comprising an effective cell differentiating amount of one or more butyryl glycerides and a pharmaceutically acceptable carrier.

This invention also provides a method of treating leukemia in a subject by administration to the subject of one or more oral bolus doses of a pharmaceutical composition comprising an effective amount of one or more butyryl glycerides and a pharmaceutically acceptable carrier effective to treat leukemia.

This invention also provides a method of treating thalassemia in a subject by administration to the subject of one or more oral bolus doses of a pharmaceutical composition comprising an effective amount of one or more butyryl glycerides and a pharmaceutically acceptable carrier effective to treat thalassemia.

This invention further provides a method of treating sickle cell anemia in a subject by administration to the subject of one or more oral bolus doses of a pharmaceutical composition comprising an effective amount of one or more butyryl glycerides and a pharmaceutically acceptable carrier effective to treat sickle cell anemia.

Lastly, this invention provides a method of treating a surface or skin disorder in a subject by topical administration to the subject of a pharmaceutical composition comprising an effective amount of one or more butyryl glycerides and a pharmaceutically acceptable carrier effective to treat the surface or skin disorder.

DETAILED DESCRIPTION

Figure 1:
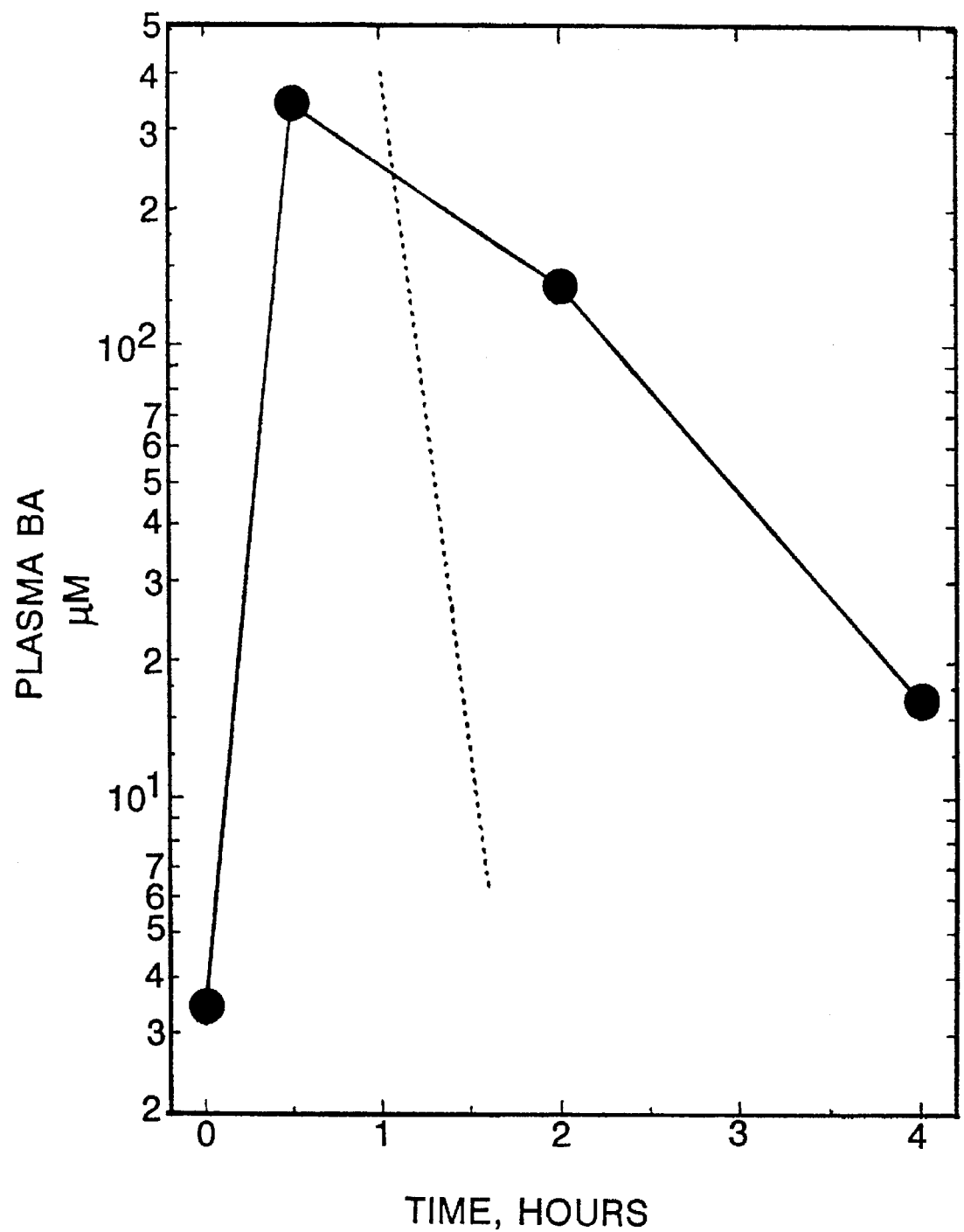
FIG. 1. The plasma concentration of butyric acid in rats fed 1 gm of tributyrin (●—●), half-life of about 40 minutes, as compared to the plasma concentration of sodium butyrate in humans and rabbits ( - - - ), half-life of about 6 minutes.

This invention provides a method of inducing cell differentiation in a subject by administration to the subject of one or more oral bolus doses of a pharmaceutical composition comprising an effective cell differentiating amount of one or more butyryl glycerides and a pharmaceutically acceptable carrier.

As used herein, the term "butyryl glycerides" means any butyric acid esters of glycerol which, when administered to a subject, will deliver and maintain a pharmacologically effective amount of butyrate in the subject for a sufficient amount of time in order to effectively induce cell differentiation. Examples of butyryl glycerides are known to those skilled in the art and include, but are not limited to, tributyryl glyceride as well as various dibutyryl glycerides or monobutyryl glycerides.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

In the practice of this invention the amount of the compound incorporated in the composition may vary. Factors considered when determining the precise amount are well known to those skilled in the art. Examples of such factors include, but are not limited to, the subject being treated, the specific pharmaceutical carrier and route of administration being employed and the frequency with which the composition is to be administered.

In a preferred embodiment of the invention, an effective cell differentiating amount of one or more butyryl glycerides is an amount totaling between 1 and 50 grams per dose.

In one embodiment, the pharmaceutical composition of this invention is administered in conjunction with other pharmaceutical agents which passes activity as gastrointestinal lipase inhibitors to reduce lipase hydrolysis of the glycerides in the gastrointesinal tract, and thus enhance effective absorption of the glycerides. Examples of gastrointestinal lipase inhibitors are well known to those skilled in the art and include, but are not limited to, the Roche compound RO-18-0647 (Orlistat R$^+$).

This invention also provides a method of treating leukemia in a subject by administration to the subject of one or more oral bolus doses of a pharmaceutical composition comprising an effective amount of one or more butyryl glycerides and a pharmaceutically acceptable carrier effective to treat leukemia.

As used herein, the term "butyryl glycerides" means any butyric acid esters of glycerol which, when administered to a subject having leukemia, will deliver and maintain a pharmacologically effective amount of butyrate in the subject for a sufficient amount of time in order to effectively treat leukemia. Examples of butyryl glycerides are known to those skilled in the art and include, but are not limited to, tributyryl glyceride as well as various dibutyryl glycerides or monobutyryl glycerides.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the practice of this invention the amount of the compound incorporated in the composition may vary. Factors considered when determining the precise amount are well known to those skilled in the art. Examples of such factors include, but are not limited to, the subject being treated, the specific pharmaceutical carrier and route of administration being employed and the frequency with which the composition is to be administered.

In a preferred embodiment of the invention, an effective amount of one or more butyryl glycerides effective to treat leukemia is an amount totaling between 1 and 50 grams per dose.

In one embodiment, the pharmaceutical composition of this invention is administered in conjunction with other pharmaceutical agents which posses activity as gastrointestinal lipase inhibitors to reduce lipase hydrolysis of the glycerides in the gastrointesinal tract, and thus enhance effective absorption of the glycerides. Examples of gastrointestinal lipase inhibitors are well known to those skilled in the art and include, but are not limited to, the Roche compound RO-18-0647 (Orlistat R$^+$).

This invention also provides a method of treating thalassemia in a subject by administration to the subject of one or more oral bolus doses of a pharmaceutical composition comprising an effective amount of one or more butyryl glycerides and a pharmaceutically acceptable carrier effective to treat thalassemia.

As used herein, the term "butyryl glycerides" means any butyric acid esters of glycerol which, when administered to a subject, will deliver and maintain a pharmacologically effective amount of butyrate in the subject for a sufficient amount of time in order to effectively treat thalassemia. Examples of butyryl glycerides are known to those skilled in the art and include, but are not limited to, tributyryl glyceride as well as various dibutyryl glycerides or monobutyryl glycerides.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the practice of this invention the amount of the compound incorporated in the composition may vary. Factors considered when determining the precise amount are well known to those skilled in the art. Examples of such factors include, but are not limited to, the subject being treated, the specific pharmaceutical carrier and route of administration being employed and the frequency with which the composition is to be administered.

In a preferred embodiment of the invention, an effective amount of one or more butyryl glycerides effective to treat thalassemia is an amount totaling between 5 and 50 grams per dose.

In one embodiment, the pharmaceutical composition of this invention is administered in conjunction with other pharmaceutical agents which passes activity as gastrointestinal lipase inhibitors to reduce lipase hydrolysis of the glycerides in the gastrointesinal tract, and thus enhance effective absorption of the glycerides. Examples of gastrointestinal lipase inhibitors are well known to those skilled in the art and include, but are not limited to, the Roche compound RO-18-0647 (Orlistat R+).

This invention also provides a method of treating sickle cell anemia in a subject by administration to the subject of one or more oral bolus doses of a pharmaceutical composition comprising an effective amount of one or more butyryl glycerides and a pharmaceutically acceptable carrier effective to treat sickle cell anemia.

As used herein, the term "butyryl glycerides" means any butyric acid esters of glycerol which, when administered to a subject, will deliver and maintain a pharmacologically effective amount of butyrate in the subject for a sufficient amount of time in order to effectively treat sickle cell anemia. Examples of butyryl glycerides are known to those skilled in the art and include, but are not limited to, tributyryl glyceride as well as various dibutyryl glycerides or monobutyryl glycerides.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the practice of this invention the amount of the compound incorporated in the composition may vary. Factors considered when determining the precise amount are well known to those skilled in the art. Examples of such factors include, but are not limited to, the subject being treated, the specific pharmaceutical carrier and route of administration being employed and the frequency with which the composition is to be administered.

In a preferred embodiment of the invention, an effective amount of one or more butyryl glycerides effective to treat sickle cell anemia is an amount totaling between 1 and 50 grams per dose.

In one embodiment, the pharmaceutical composition of this invention is administered in conjunction with other pharmaceutical agents which passes activity as gastrointestinal lipase inhibitors to reduce lipase hydrolysis of the glycerides in the gastrointesinal tract, and thus enhance effective absorption of the glycerides. Examples of gastrointestinal lipase inhibitors are well known to those skilled in the art and include, but are not limited to, the Roche compound RO-18-0647 (Orlistant R+).

This invention further provides a method of treating a surface or skin disorder involving hyperproliferating and abnormal cells in a subject by topical administration to the subject of a pharmaceutical composition comprising an effective amount of one or more butyryl glycerides and a pharmaceutically acceptable carrier effective to treat the surface or skin disorder.

As used herein, the term "butyryl glycerides" means any butyric acid esters of glycerol which, when administered to a subject, will deliver and maintain a pharmacologically effective amount of butyrate in the subject for a sufficient amount of time in order to effectively treat sickle cell anemia. Examples of butyryl glycerides are known to those skilled in the art and include, but are not limited to, tributyryl glyceride as well as various dibutyryl glycerides or monobutyryl glycerides.

Examples of surface or skin disorders against which the pharmaceutical composition of this invention would be useful are well known to those skilled in the art. Examples include, but are not limited to dermatitis, eczema, psoriasis, lack of adequate skin firmness, dermal hydration, sebum secretion or leukoplakia.

In a preferred embodiment of this invention, the effective cell differentiating amount of one or more butyryl glycerides is an amount between 1 and 50 grams per dose.

Topical administration can be effected by any method commonly known to those skilled in the art which include, but are not limited to, incorporation of the pharmaceutical composition into creams, ointments or transdermal patches.

In a preferred embodiment the pharmaceutical composition of this invention further comprises a substance having Vitamin D activity. As used herein, the term "Vitamin D activity" means any compound which exhibits the same antirachitic activity as Vitamin $D_2$ or Vitamin $D_3$. Those skilled in the art will recognize that ultraviolet radiation of a variety of animal and plant sterels, including but not limited to 7-dehydrocholesterol or ergosterol, result in their conversion to compounds with antirachitic activity. [Goodman and Gilman's "The Pharmacological Basis of Therapeutics," 8th Edn., (Gilman et al. eds.) (Pergamon Press, New York: 1990) pages 1510–1517]. Substances having Vitamin D activity are well known to those skilled in the art. Examples include, but are not limited to, calciferol, calcitriol (1,25-dihydroxycholecalciferol) or active analogs or derivatives thereof including, but not limited to, dihydrotachysterol or 1-hydroxy-cholecalciferol. Further examples of compounds having Vitamin D activity will become apparent to those skilled in the art and it is anticipated that these are also within the scope of this invention.

This invention is further illustrated in the Experimental Details section which follows. The Experimental Details section is set forth to aid in an understanding of the invention but is not intended to, and should not be construed to, limit in any way the invention as set forth in the claims which follow thereafter.

EXPERIMENTAL DETAILS

Example 1

Three male Sprague Dawley rats (Harlan Sprague Dawley, Houston, Tex.) weighing approximately 306 g were fasted overnight and gavaged with 1 gm of tributyrin (Sigma catalog #T-5142, 99% pure, 302.4M) directly into the stomach. A fourth rat-was not gavaged. Rats were sacrificed at time zero (without gavage) or 0.5, 2 and 4 hours post gavage. At time of sacrifice, each rat was anesthetized with a mixture of ketamine (87 mg/kg) and rompun (13 mg/kg). A cardiac puncture was performed and approximately 2 mls of blood was withdrawn into a heparinized vacutainer tube. Blood was centrifuged at 2000×g for 7 minutes and plasma was withdrawn and stored frozen until analysis. At the time of analysis, plasma concentration was determined by the method of Remsey and Demigne (1974) using chromatographic methods as described by Boffa et al. (1992).

Results

As shown in the following Table 1, plasma butyrate concentrations were:

Time zero 3.39 µM 0.5 hours 336.32 µM 2 hours 135.88 µM 4 hours 16.27 µM

It appears that butyrate is very rapidly absorbed and is almost back to baseline at 4 hours.

TABLE 1

EFFECT OF TRIBUTYRIN INTUBATION ON BLOOD LEVELS OF BUTYRATE

| | STANDARDS | | | |
|---|---|---|---|---|
| | M MOLAR STD | RETENTION | INTENSITY STD | R FACTOR |
| INTERNAL STD | 0.482 | 3.493 | 1198 | |
| ACETIC | 0.982 | 2.792 | 1365 | 0.4154 |
| PROPIONIC | 0.489 | 3.3 | 797 | 0.3543 |
| BUTYRIC | 0.481 | 4.013 | 1126 | 0.2467 |

| SAMPLE STD | WT (g) | M | VOL | PU | mM |
|---|---|---|---|---|---|
| ISOBUTYRIC | 0.01799 | 88.10 | 0.05 | 99 | 4.125 |

(internal standard, i.s.)

| | SAMPLES | | | |
|---|---|---|---|---|
| | RETENTION | INTENSITY | AMOUNT (μMOLES) | SAMPLES CONC (μM) |
| SAMPLE # 0 HR | | | | |
| ACETIC | 2.786 | 3852 | 0.0070 | 34.8861 |
| PROPIONIC | 3.005 | 3814 | 0.0059 | 29.4590 |
| BUTYRIC | 4.142 | 631 | 0.0007 | 3.3933 |
| ISOBUTYRIC (i.s.) | 3.488 | 18922 | 0.0825 | |
| SAMPLE # 0.5 HR | | | | |
| ACETIC | 2.785 | 1049 | 0.0091 | 45.3040 |
| PROPIONIC | 3.005 | 1960 | 0.0137 | 68.5087 |
| BUTYRIC | 4.005 | 13115 | 0.067 | 336.3235 |
| ISOBUTYRIC (i.s.) | 3.486 | 3968 | 0.0825 | |
| SAMPLE # 2 HR | | | | |
| ACETIC | 2.78 | 5235 | 0.0140 | 70.0217 |
| PROPIONIC | 3.003 | 6912 | 0.0158 | 78.8481 |
| BUTYRIC | 3.996 | 17109 | 0.0272 | 135.8840 |
| ISOBUTYRIC (i.s.) | 3.479 | 12812 | 0.0825 | |
| SAMPLE # 4 HR | | | | |
| ACETIC | 2.775 | 2167 | 0.0084 | 42.1709 |
| PROPIONIC | 3.003 | 3276 | 0.0109 | 54.3713 |
| BUTYRIC | 3.99 | 1408 | 0.0033 | 16.2699 |
| ISOBUTYRIC (i.s.) | 3.474 | 8806 | 0.0825 | |

Discussion

A single oral dose bolus of 1 gm of tributyrin was administered to rats, and the plasma levels of free butyrate measured over 4 hours. The results indicated:

1. A peak level of 0.35 mM butyrates.
2. A half-life of about 40 minutes.

The results were surprising, in that the peak blood level, the time over 0.10 mM (about 2 hours) and the much slower half-life of 40 minutes could not be achieved with the previous butyrate salts used, even by intravenous infusion. This approach thus opens the route to oral administration of tributyrin as a means of obtaining effective free butyrates in blood levels for a practical period of time. Repeated oral doses could obviously maintain an effective level for practical treatment use.

Topical application of one or more of the glycerides could also be useful in treating surface and skin disorders involving hyperproliferating and abnormal cells. This effect could be particularly useful in conjunction with a substance of Vitamin D activity, such as 1.25 dihyroxycholecalciferol (calcitriol) or its active analogues. This is based on extensive known literature of additive or synergistic effects of combinations of sodium butyrate and active Vitamin D forms in affecting differentiation of a variety of cancer or transformed cells lines. Butyryl glycerides are far more suitable for topical application in such systems since they do not contain the troublesome sodium ion, are un-ionized themselves, and as such, are more readily absorbed on topical application.

References

1. Perrine S. P., et al., A short-term trial of butyrate to stimulate fetal-globingene expression in the β-globin disorders. N. Engl. J. Med. 328:81–86, 1993.
2. Perrine, S. P., et al., Sodium butyrate enhance fetal globin gene expression in erythroid progenitors of patients with Hb SS and β-thalassemia. Blood 74:454–459, 1989.
3. Novogrodsky, A., et al., Effect of polar organic compounds on leukemia cells. Butyrate-induced partial remission of acute myelogenous leukemia in a child. Cancer 11:9–14.
4. Miller, A. A., et al., Clinical pharmacology of sodium butyrate in patients with acute leukemia. Eur. J. Cancer Clin. Oncol. 23:1283–1287, 1987.
5. Cummings, J. H., Short chain fatty acids in the human colon. Gut, 22, 763–779, 1981.
6. Composition of Foods: Dairy and Egg Products (1976), U.S. Dept. Agriculture Handbook 8-1, Washington, D.C.

7. Deschner, et al., Dietary butyrate(tributyrin) does not enhance AOM-induced colon tumorigenesis. Cancer Letters 52:79–82, 1990.
8. Freeman, H. J., Effects of differing concentrations of sodium butyrate on 1,2-dimethylhydraxine-induced rat intestine neoplasia. Gastroenterology, 91:596–602, 1986.
9. Lea, M. A. et al., Butyramide and monobutyrin: Growth inhibitory and differentiation agents. Anticancer Res., 13:145–150, 1993.
10. Boffa, et al., Modulation of colonic epithelial cell proliferation, histone acetylation and luminal short chain fatty acids by variation of dietary fiber (wheat bran) in rats. Cancer Research 52:5906–5912, 1992.
11. Remesy, C. and Demigne, C., Determination of volatile fatty acids in plasma after ethanolic extraction. Biochem. J. 141:85–91, 1974.
12. Goodman and Gilman's "The Pharmacological Basis of Therapeutics," 8th Edn., (Gilman et al. eds.) (Pergamon Press, New York: 1990) pages 1510–1517.

What is claimed:

1. A method of inducing cell differentiation in a subject by administration to the subject of one or more oral bolus doses of a pharmaceutical composition comprising an effective cell differentiating amount of tributyrin and a pharmaceutically acceptable carrier.

2. The method of claim 1, wherein the effective cell differentiating amount of tributyrin is an amount between 1 and 50 grams per dose.

3. A method of achieving butyrate concentrations of at least 50 µM to 35 mM in the plasma of a subject in need thereof which comprises administering to the subject one or more oral bolus doses of a pharmaceutical composition comprising tributyrin in the range of 1 gram to 50 grams per dose and a pharmaceutically acceptable carrier.

* * * * *